United States Patent [19]

Rosenthal

[11] Patent Number: 4,850,365
[45] Date of Patent: Jul. 25, 1989

[54] NEAR INFRARED APPARATUS AND METHOD FOR DETERMINING PERCENT FAT IN A BODY

[75] Inventor: Robert D. Rosenthal, Gaithersburg, Md.

[73] Assignee: Futrex, Inc., Gaithersburg, Md.

[21] Appl. No.: 167,711

[22] Filed: Mar. 14, 1988

[51] Int. Cl.$^4$ ............................................. A61B 6/00
[52] U.S. Cl. ................................... 128/664; 128/633; 250/341; 250/339
[58] Field of Search .............. 128/632, 633, 634, 664; 250/339, 341; 356/445, 446, 447

[56] References Cited

U.S. PATENT DOCUMENTS

| | | | |
|---|---|---|---|
| 4,515,165 | 5/1985 | Carroll | 128/664 |
| 4,570,638 | 2/1986 | Stoddort et al. | 128/665 |
| 4,633,087 | 12/1986 | Rosenthal et al. | 250/341 |
| 4,768,516 | 9/1988 | Stoddort et al. | 128/664 |

OTHER PUBLICATIONS

Stokes et al., Metabolic Complications of Human Obesities; Elsevier Science Publishers, B.V. (Biomedical Division); J. Vague et al., eds.; pp.49–57.
Conway et al., The American Journal of Clinical Nutrition, 40, Dec. 1984, pp. 1123–1130.

*Primary Examiner*—Lee S. Cohen
*Assistant Examiner*—John C. Hanley
*Attorney, Agent, or Firm*—Bernard, Rothwell & Brown

[57] ABSTRACT

Method and apparatus for determining percent fat in a body wherein substantially uniformly dispersed near-infrared radiation is transmitted into the body to achieve optical interactance between the body and the near-infrared radiation. Optical absorption by the body at only one wavelength of the near-infrared radiation is measured. The measured absorption at the one wavelength of near-infrared radiation is utilized to quantitatively determine the fat content of the body. Data on a plurality of physical parameters of the body, such as height, weight, exercise level, sex, race, waste-to-hip measurement and arm circumference, can be utilized along with the measured near-infrared absorption in the quantitative determination of body fat content.

26 Claims, 3 Drawing Sheets

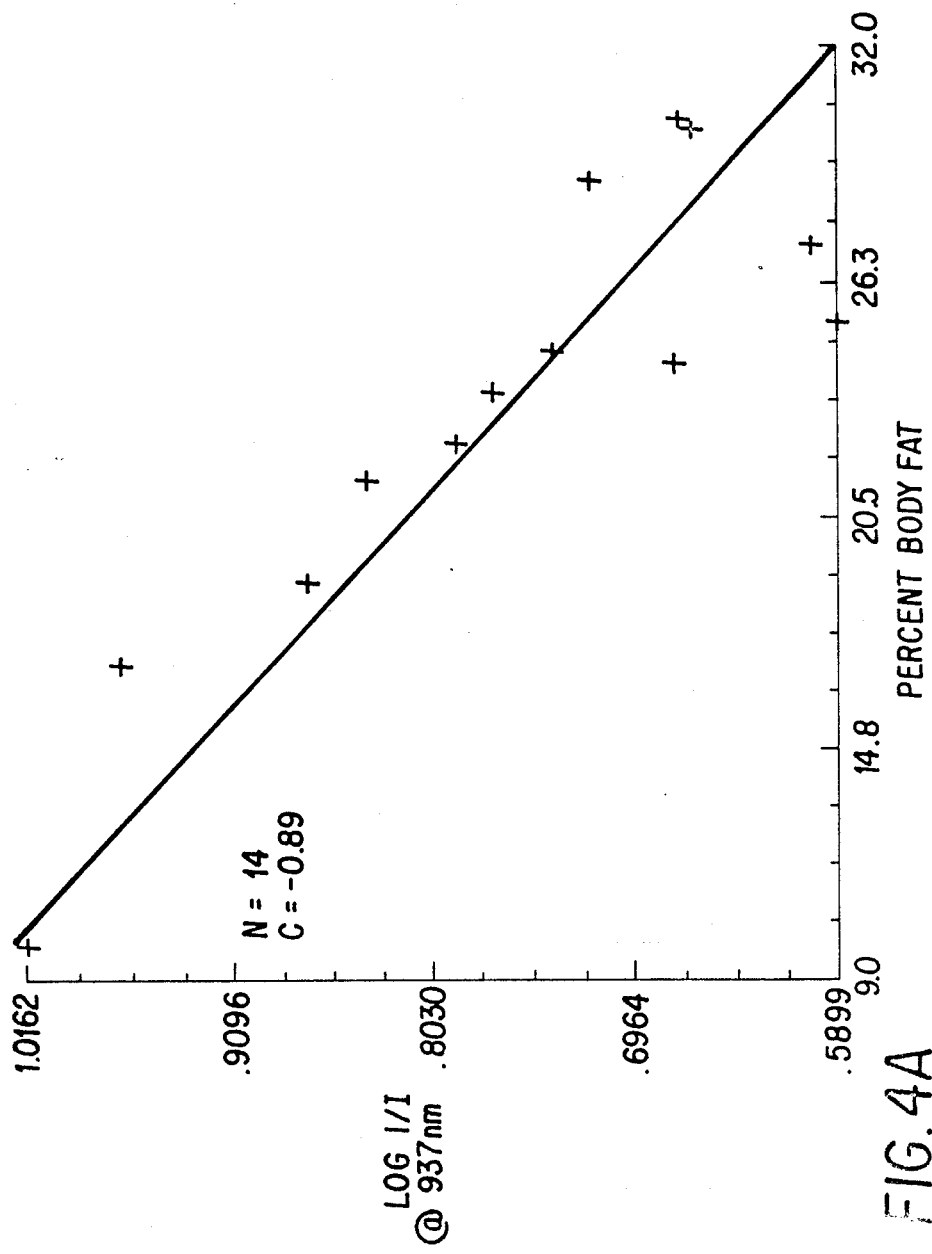

NEAR INFRARED APPARATUS AND METHOD FOR DETERMINING PERCENT FAT IN A BODY

BACKGROUND OF THE INVENTION

1. Field of the Invention

The present invention relates to improvements in instruments and methods for performing near infrared quantitative analysis to determine percent fat in a body.

2. Description of the Background Art

It has long been known that obesity reduces longevity, and recent studies have demonstrated that high percentage of body fat is an independent health risk factor as a cause of heart attack, stroke, diabetes and other disabling diseases. (Stokes et al, *Metabolic Complications of Human Obesities;* Elsevier Science Publishers, B.V. (Biomedical Division); J. Vague et al, eds.; pp. 49–57 [1985]).

For the above reasons, several techniques have been developed to determine percent body fat, including recent techniques based on USDA research that demonstrates that "near-infrared light interactance" can provide the basis for measurement of percent body fat (Conway et al, *The American Journal of Clinical Nutrition* 40:1123–1130 [1984]).

Near-infrared light interactance technology disclosed in U.S. Pat. No. 4,633,087 to Rosenthal et al has recently been utilized in a commercial instrument for measurement of body composition, i.e., percent fat in the human body. However, because of the cost required to manufacture an instrument that utilizes this technology, the majority of purchasers are health clubs, medical centers and sports teams, with only a very small percentage of buyers being individual consumers.

Taking full advantage of the technology disclosed in U.S. Pat. No. 4,633,087 requires the measurement of more than one wavelength in the near-infrared spectrum. The reason for this is that what is being measured is the change in slope of the absorption curve, with the slope being defined as the difference in optical absorption at two defined wavelengths.

For the following reasons, the cost of utilizing the technology described in U.S. Pat. No. 4,633,087 remains high even when utilizing inexpensive infrared emitting diodes (IREDs) as the near-infrared source:

(1) The use of two IREDs are preferred for each of two wavelengths being measured, and the more IREDs that are used, the greater the expense.

(2) An electronic means for turning on and off each pair of IREDs in a sequential fashion and keeping them on for a predetermined length of time is required.

(3) Circuitry is required that allows the output of the pairs of IREDs to be adjusted so that they have equal energies when measuring a neutral sample.

(4) Computation circuitry is required that must not only discriminate between two pairs of IREDs, but also perform a multiple regression calculation.

(5) Instrument display capability is required that has the ability to read-out each of the two pairs of IREDs, as well as the final percent fat.

(6) The instrument must also have the ability of entering a multiple number of constants because of the multi-term linear regression equation utilized.

In view of the costs required in providing known devices for measuring body fat content, there remains a need in the art for improved and less expensive devices for measuring percent body fat.

SUMMARY OF THE INVENTION

In accordance with the present invention, a method for determining percent fat in a body comprises transmitting substantially uniformly dispersed near-infrared radiation into a body to achieve optical interactance between the body and the near-infrared radiation. Optical absorption by the body of the near-infrared radiation is measured at only one wavelength of the near-infrared radiation. The measured absorption at that one wavelength of the near-infrared radiation is utilized to quantitatively determine the fat content of the body. Data on a plurality of physical parameters of the body, such as height, weight, exercise level, sex, and race, may be utilized along with the measured absorption, to quantitatively determine the fat content of the body. The invention further relates to an apparatus for carrying out the above-described method.

BRIEF DESCRIPTION OF THE DRAWINGS

FIG. 4A graphically shows optical density at 937 nanometers of the biceps of fourteen human subjects, versus percent body fat.

DETAILED DESCRIPTION OF THE PREFERRED EMBODIMENTS

The invention provides a method and apparatus for determining percent body fat utilizing optical interactance principles in the near-infrared radiation wavelength range of from about 740 to about 1100 nanometers. Because of a previously unknown relationship between optical density (O.D.) and percent body fat, a single O.D. measurement can be utilized to provide a high correlation with percent body fat. Optical density is defined as log 1/I, wherein I is interactance and equal to $E_s/E_r$ ($E_s$=energy received from subject; $E_r$=energy received from a reference). When taking a measurement halfway between the shoulder and elbow on the bicep of a person's prominent arm (the one used for writing), the local amount of fat measured is directly proportional to the total fat in the body. With the present invention, a single wavelength measurement can provide meaningful measurement of percent total body fat. A single wavelength is able to provide this measurement since the higher the percent body fat, the more transparent the arm of the subject. This is because low body fat people have "hard muscles" that make it difficult for light to penetrate, therefore providing high O.D. values. Conversely, people with high percent body fat have a "flabby" bicep that is not very optically dense, resulting in low O.D. values.

Figure 1:
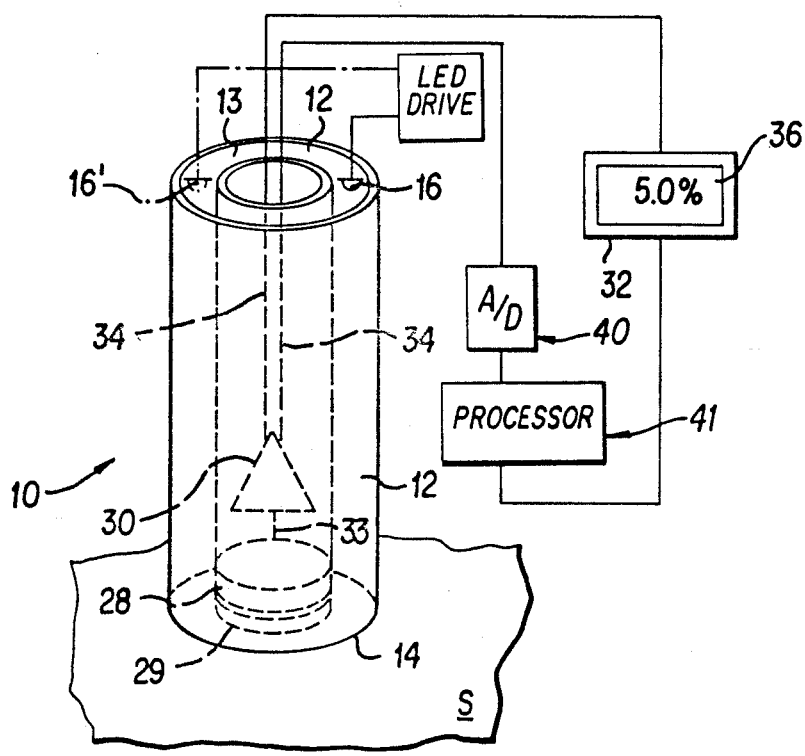
FIG. 1 is a partially schematic perspective view of an instrument according to the invention.

Although there are some similarities between an apparatus in accordance with the present invention and that disclosed in U.S. Pat. No. 4,633,087 (incorporated herein by reference), there are significant differences between the two. As shown in FIG. 1, the probe portion 10 of the instrument of the invention is of hollow cylindrical form and includes a hollow tubular member 12 having a wall of solid translucent material selected so that it transmits and does not substantially or inconsistently absorb near-infrared energy in the bandwidth of interest, namely, from about 740 to about 1100 nanometers. Examples of suitable materials out of which tubular member 12 may be constructed include, but are not limited to, translucent nylon, translucent polytetrafluoroethylene and the like. Means for providing a point source of near-infrared radiation of a predetermined wavelength is positioned at an upper end portion 13 of tubular member 12. The near-infrared point source means at the upper end portion 13 of tube 12 is positioned so that near-infrared radiation of the predetermined wavelength emitting from the point source means will be transmitted by the tubular member 12 from the upper end portion 13 to a flat bottom surface 14 of tube 12. The near-infrared point source means preferably comprises infrared emitting diode (IRED) means 16.

Although there is no need to be particularly specific in the wavelength of interest that the IRED emits, so long as it is within the near-infrared spectrum, the larger the half-power bandwidth of the light source, within reason, the better the measurement, since less interference from other body parameters occurs. Thus, the use of a conventional 950 nanometer IRED as the illumination source is almost ideal. Such infrared-emitting diodes have half-power bandwidths of almost 60 nanometers, which make them practically immune to other types of absorptions (e.g., absorption due to moisture, protein, etc.).

In preferred embodiments, light transmitting tube 12 is made a suitable length to provide sufficient internal light scattering to smooth out the emitted light so that light from the IRED is transmitted through tube 12 and emerges uniformly at the bottom surface 14 of the tube.

Most preferably, the tube 12 is no longer than is necessary to uniformly smooth out the light emitted from the IRED, in order to minimize the loss of near-infrared radiation. The ideal tube length can be easily determined by utilizing a commercially available infrared viewer (nightscope). A tube may be sized by observing near-infrared radiation passing through the tube and trimming the tube until the light emerges uniformly. A silicon detector is then passed around the end of the tube to check for uniform output.

The tube can be shorter than is required for uniform light emergence. If the tube length is such that non-uniform light emerges from the end of the tube, consistent results can still be obtained if the tube is oriented in the same direction for each reading, so that the non-uniformity of emerging light will be consistently read.

Since only one IRED is required, to achieve desirably uniform light emergence, tube 12 must be longer than that described in U.S. Pat. No. 4,633,087, e.g., about 1.5 times longer than when using a pair of IREDs. Longer tube length is acceptable since a single wavelength measurement does not require the precision that is required in the preferred embodiment of the above-described patent. When a two wavelength measurement is made, as in the preferred embodiment of U.S. Pat. No. 4,633,087, a small change in the energy between the two wavelengths must be resolved. Thus, to make an accurate measurement of body fat, a two wavelength measurement requires the ability to resolve approximately 0.001 difference between optical density (log 1/I values) at two wavelengths. Thus, the precision of the measurement must be relatively high, requiring a twelve bit analog-to-digital converter.

Figure 4B:
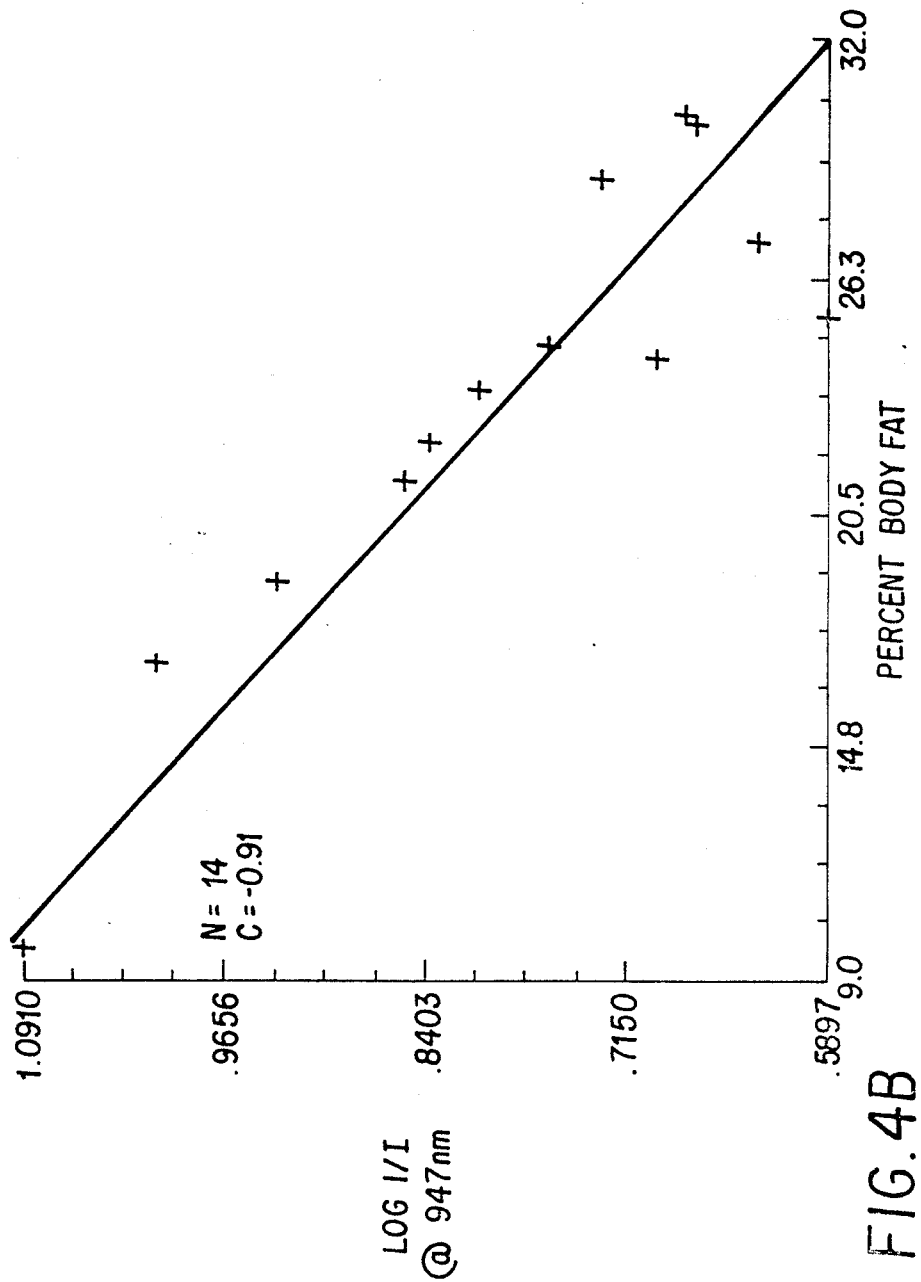
FIG. 4B graphically shows optical density at 947 nanometers of the biceps of fourteen human subjects, versus percent body fat.

FIGS. 4A and 4B represent single wavelength measurements for fourteen subjects in accordance with the present invention at 937 nanometers and 947 nanometers, respectively, and show the negative correlation of percent body fat and optical density. In a single wavelength measurement in accordance with the present invention, the resolution can be at least ten times less stringent, and perhaps as much as one hundred times less stringent, than is required using a two wavelength measurement (i.e., an eight-bit analog-to-digital conversion is acceptable). Thus, the lower resolution means allows a lower light level, which in turn permits the use of a single IRED in conjunction with a longer light tube 12. If desired, however, more than one IRED emitting the same wavelength can be used to increase the light level, such as IREDs 16, 16', but it is only necessary to measure absorbence at a single wavelength emitted by both diodes.

For light shielding purposes, the cylindrical walls of tubular light transmitting member 12 are shielded on the outside by an outer tubular opaque shield 20 and on the inside by inner tubular opaque shield 22. The upper end portion 13 of tubular member 12 is also shielded from ambient light by a top cover, not shown.

Figure 2:
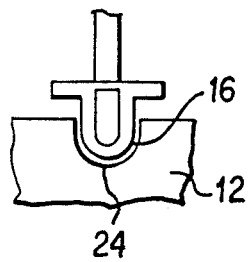
FIG. 2 is a detailed sectional, partially schematic view of a portion of the instrument of FIG. 1 showing IRED positioning.

In the embodiment shown, IRED 16 is positioned in a depression 24 in the top surface of the upper end portion 13 of light-transmitting tube 12. See FIG. 2.

Figure 3:
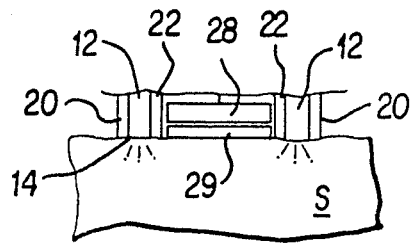
FIG. 3 is a detailed sectional, partially schematic, elevation view of the lower end of the instrument shown in FIG. 1.

An optical detector 28, capable of detecting near-infrared radiation, is positioned inside of and at the bottom end portion of the tubular member 12 as shown in FIGS. 1 and 3. Inner tubular shield 22 is positioned between detector 28 and transmitting tube 12, thereby providing an opaque mask which prevents near-infrared radiation from tube 12 from impinging directly on detector 28. Optical detector 28 generates an electrical signal when the detector detects light.

The optical detector 28 is connected to the input of an electrical signal amplifier 30 by suitable electrical conducting means 33. Amplifier 30 may be an inexpensive signal amplifier, and amplifies signals generated by detector 28 in response to light detected by the detector. The detector 28 preferably is positioned within tube 22. The output of amplifier 30 feeds the amplified signal generated by detector 28 to a readout box 32 through conductive lines 34. The readout box 32 may have a display 36 for directly reading the percentage of fat in a test subject S.

A near-infrared-transparent window 29 is located in front of the optical detector 28. If desired, window 29 can be electrically conductive and grounded directly to the apparatus electronics to provide shielding from electro-magnetic interferences that are commonly encountered in industrial and consumer premises. However, acceptable results are achievable when using non-electrically conductive windows.

The output of amplifier 30 is fed to an integrating analog-to-digital converter 40 having an eight bit output, which is connected to a digital processor 41 connected to readout box 36.

The data processing and readout means connected to amplifier 30 are capable of processing the amplified signal resulting from detection of only a single, predetermined wavelength, to provide a readout indicative of the percent fat in the body based on the detection of that single, predetermined wavelength.

This invention utilizes the principal of interactance, which principle is known in the art and differs from reflectance and transmittance. In interactance, light from a source is shielded by an opaque member from a detector and interactance of the light with the test subject is then detected by the detector.

Since the present invention measures only a single wavelength (which may be emitted from only a single IRED), there is no need for the instrument to cycle on and off, as is required when utilizing multiple wavelength measurements. Thus, there is no need for the inclusion of a timing circuitry nor IRED cycling circuitry, as is provided in a multiple wavelength instrument.

In operation, the bottom surface 14 and window 29 are positioned against a surface of test subject S. Substantially uniformly dispersed near-infrared radiation emerging from end 14 is transmitted into the body of test subject S to achieve optical interactance between the body and the near-infrared radiation. Near-infrared radiation is detected by detector 28, and optical absorption by the body at only one predetermined wavelength of the near-infrared radiation is measured. Detector 28 then generates an electrical signal representing the measured absorption at only the one predetermined wavelength, which is thereafter utilized to quantitatively determine the fat content of the body.

With only a single wavelength measurement, a simple slope/bias computation is all that is required to directly determine percent fat. Accordingly, the computation required with single wavelength measurement is considerably simpler, and less costly to implement, than the computation required with multiple wavelength measurement. With single wavelength measurement, the equation can be as simple as:

% body fat=$K_0+K_1(1/I)$ wherein I is as defined above, $K_0$ represents an intercept error constant and $K_1$ represents a line slope constant, both constants being determined by multiple regression techniques, i.e., optical readings are obtained from the components of the instrument being constructed for a representative number of samples which have been previously accurately analyzed, and the optical readings and previously measured percentages are utilized to calculate sets of constant values for fat content using a conventional regression algorithm in a digital computer. The respective K values are then programmed into the analyzing instrument being constructed so that the instrument can directly compute percentage fat from optical data readings.

Performing the analysis on a linear basis in accordance with the equation immediately above substantially reduces the cost of the instrument, but also results in a considerable decrease in accuracy. The accuracy of the measurement can be greatly increased by performing the analysis according to the following equation:

% body fat=$K_0+K_1(\log 1/I)$ wherein $K_0$, $K_1$ and I are as defined above.

As noted above, the single measurement can be made using an IRED at almost any near-infrared center wavelength. However, people of African origin have flesh pigments that absorb light from the visible portion of the spectrum through the very near-infrared spectrum, disappearing at about 950 nanometers. Thus, the commercially available low-cost IREDs at 950 nanometers are practically ideal, since they avoid a substantial effect in the measurement based on skin color.

To provide even more accurate determination of percent body fat, data on a plurality of physical parameters of the body can be utilized along with the measured absorption of near-infrared radiation, to quantitatively determine the fat content of a body. Such physical parameters include, but are not limited to height, weight, exercise level, sex, race, waste-to-hip measurement, and arm circumference. When utilizing data on physical parameters in conjunction with measurement of near-infrared absorption in a single wavelength measurement, a suitable equation is as follows:

% body fat=$K_0+K_1(\log 1/I)+K_3(W/100)$
$+K_4(H/100)+K_5(S)+K_6(EL)$ wherein $K_0$, $K_1$ and I are as defined above. W is weight in pounds; H is height in inches; S is sex (male=+0.01, female=−0.01); EL is exercise level: none equals 0; light=0.02; moderate=0.05; heavy=0.08. $K_3$−$K_6$ are constants which are determined by multiple regression techniques as described above, i.e., optical readings are obtained from the components of the instrument being constructed for a representative number of samples that have been accurately analyzed, and the optical readings and previously measured percentage are utilized to calculate sets of $K_3$−$K_6$ values for the respective body parameters using a conventional regression algorithm in a digital computer. These sets of $K_3$−$K_6$ values are then programmed into the analyzing instrument being constructed so that the instrument can directly compute the percentage body fat (taking into consideration both the optical data readings and the data on the physical parameters of the body of a particular subject.)

Data on a plurality of physical parameters of the body can also be utilized in conjunction with multiple wavelength measurement of near-infrared absorbance, as in prior U.S. Pat. No. 4,633,087, in accordance with the following formula:

$$\% \text{ body fat} = K_o + K_{2A}(\log 1/I_1) + K_{2B}(\log 1/I_2) + K_3(W/100) + K_4(H/100) + K_5(S) + K_6(EL)$$

wherein W, H, S and EL are as defined above; $K_0$ and $K_3$-$K_6$ are as defined above; and $K_{2A}$ and $K_{2B}$ are the respective slopes of curves representing two wavelengths being measured, and are determined by multiple regression techniques as described above. $I_1$ is interactance at one of the two wavelengths being measured, and $I_2$ is interactance at the other of the two wavelengths being measured. According to this embodiment, one of said wavelengths preferably is about 937 nanometers plus or minus about 2 nanometers, and the other of said wavelengths preferably is about 947 nanometers plus or minus about 2 nanometers, with a minimum of about 10 nanometers between said two wavelengths.

Actual K values for two instruments constructed utilizing multiple wavelength technology in accordance with the formula immediately above are set forth in Table I below:

TABLE I

|  | INSTRUMENT A | INSTRUMENT B |
|---|---|---|
| $K_0$ | 94.3 | 84.2 |
| $K_{2A}$ | −15.5 | −16.3 |
| $K_{2B}$ | −8.0 | −6.2 |
| $K_3$ | 8.3 | 8.1 |
| $K_4$ | −79.0 | −13.7 |

TABLE I-continued

|  | INSTRUMENT A | INSTRUMENT B |
|---|---|---|
| $K_5$ | −93.9 | −124.2 |
| $K_6$ | −78.7 | −81.4 |
| Correlation | .989 | .989 |
| Std. deviation | .951 | .987 |
| Figure of Merit | 13.5 | 13.0 |

The present invention provides a method and means for accurately and reliably measuring percent body fat, that is substantially less expensive than with previously known technology, and in a non-destructive manner, using near-infrared radiation interactance principles.

Since many modifications, variations and changes in detail may be made to the described embodiments, it is intended that all matter in the foregoing description and shown in the accompanying drawings be interpreted as illustrative and not in a limiting sense.

What is claimed is:

1. A method for determining percent fat in a body, comprising:
   (a) transmitting near-infrared radiation into a body to achieve optical interactance between the body and the near-infrared radiation;
   (b) measuring optical absorption by the body at only one wavelength of said near-infrared radiation; and
   (c) utilizing the measured absorption at said only one wavelength of near-infrared radiation to quantitatively determine the fat content of the body.

2. The method of claim 1, wherein said wavelength is within the range of about 740–1100 nanometers.

3. The method of claim 1, wherein said one wavelength is about 950 nanometers.

4. The method of claim 1, wherein data on a plurality of physical parameters of the body are utilized along with said measured absorption to quantitatively determine the fat content of the body.

5. The method of claim 4, wherein said physical parameters are selected from the group consisting of height, weight, exercise level, sex, race, waste-to-hip measurement, arm circumference and combinations thereof.

6. The method of claim 1 wherein the near-infrared radiation that is transmitted into said body is substantially uniformly dispersed prior to entering said body.

7. A method for determining percent fat in a body, comprising:
   (a) transmitting near-infrared radiation into a body to achieve optical interactance between the body and the near-infrared radiation;
   (b) measuring optical absorption of said near-infrared radiation by the body; and
   (c) quantitatively determining the fat content of the body utilizing the measured absorption of said near-infrared radiation in conjunction with data on a plurality of physical parameters of the body.

8. The method of claim 7 wherein the near-infrared radiation that is transmitted into said body is substantially uniformly dispersed prior to entering said body.

9. The method of claim 7, wherein said physical parameters are selected from the group consisting of height, weight, exercise level, sex, race, waste-to-hip measurement, arm circumference and combinations thereof.

10. The method of claim 7, wherein said near-infrared radiation is within the range of about 740–1100 nanometers.

11. The method of claim 7, wherein the optical absorption of said near-infrared radiation is measured at a plurality of different wavelengths.

12. The method of claim 11, wherein the optical absorption of said near-infrared radiation is measured at two different wavelengths.

13. The method of claim 12, wherein one of said wavelengths is about 937 nanometers plus or minus about 2 nanometers, and the other of said wavelengths is about 947 nanometers plus or minus about 2 nanometers, with a minimum of about 10 nanometers between said two wavelengths.

14. A near-infrared quantitative instrument for measuring fat content of a body, comprising:
   (a) means for providing a point source of near-infrared radiation;
   (b) a tube having a wall portion, the wall portion comprising a material which is capable of transmitting near-infrared radiation; the material having a composition which does not substantially or inconsistently absorb near-infrared radiation, the tube having first and second ends, the point source means being positioned at the first end of said tube for transmitting near-infrared radiation through the wall portion of said tube; the second end of the tube for positioning against said body; the second end of the tube peripherally defining a generally central area;
   (c) a near-infrared radiation detector positioned for detecting near-infrared radiation entering the generally central area peripherally defined by the second end of the tube, the detector being capable of providing an electrical signal upon detection of near-infrared radiation of only a single, predetermined wavelength;
   (d) means for preventing near-infrared radiation from the wall of the tube from impinging directly on said detector;
   (e) means for shielding the outside of the tube from ambient light;
   (f) means connected to the detector for amplifying an electrical signal provided by said detector; and
   (g) means for data processing and readout, the data processing and readout means being connected to the amplifier means and being capable of processing the amplified signal resulting from detection of only said single, predetermined wavelength so as to provide a readout indicative of the percent fat in the body based on detection of said single, predetermined wavelength.

15. The instrument of claim 14 wherein the tube is of a sufficient length that near-infrared radiation from point source means positioned at the first end of the tube will emerge substantially uniform at the second end of the tube.

16. The instrument of claim 15, wherein said near-infrared radiation is within the range of about 740–1100 nanometers.

17. The instrument of claim 16, wherein said near-infrared radiation is about 950 nanometers.

18. The instrument of claim 15, wherein the data processing and readout means further utilizes data on a plurality of physical parameters of the body, in conjunction with said amplified signal, to provide said readout.

19. The instrument of claim 18, wherein said physical parameters are selected from the group consisting of height, weight, exercise level, sex, race, waste-to-hip measurement, arm circumference and combinations thereof.

20. A near-infrared quantitative instrument for measuring fat content of a body, comprising:
(a) means for providing at least one point source of near-infrared radiation;
(b) a tube having a wall portion, the wall portion comprising a material which is capable of transmitting near-infrared radiation; the material having a composition which does not substantially or inconsistently absorb near-infrared radiation, the tube having first and second ends, the point source means being positioned at the first end of said tube for transmitting near-infrared radiation through the wall portion of said tube; the second end of the tube for positioning against said body, the second end of the tube peripherally defining a generally central area;
(c) a near-infrared radiation detector positioned for detecting near-infrared radiation entering the generally central area peripherally defined by the second end of the tube, the detector being capable of providing an electrical signal upon detection of near-infrared radiation;
(d) means for preventing near-infrared radiation from the wall of the tube from impinging directly on said detector;
(e) means for shielding the outside of the tube from ambient light;
(f) means connected to the detector for amplifying an electrical signal provided by said detector; and
(g) means for data processing and readout, the data processing and readout means being connected to the amplifier means and being capable of processing the amplified signal in conjunction with data on a plurality of physical parameters of said body so as to provide a readout indicative of the percent fat in the body.

21. The instrument of claim 20 wherein the tube is of a sufficient length that near-infrared radiation from point source means positioned at the first end of the tube will emerge substantially uniform at the second end of the tube.

22. The instrument of claim 21, wherein said physical parameters are selected from the group consisting of height, weight, exercise level, sex, race, waste-to-hip measurement, arm circumference and combinations thereof.

23. The instrument of claim 21, wherein said near-infrared radiation is within the range of about 740–1100 nanometers.

24. The instrument of claim 21, wherein said near-infrared radiation comprises a plurality of different wavelengths.

25. The instrument of claim 24, wherein said near-infrared radiation comprises two different wavelengths.

26. The instrument of claim 25, wherein one of said wavelengths is about 937 nanometers plus or minus about 2 nanometers, and the other of said wavelengths is about 947 nanometers plus or minus about 2 nanometers, with a minimum of about 10 nanometers between said two wavelengths.

* * * * *